United States Patent
Xu et al.

(10) Patent No.: US 6,524,571 B1
(45) Date of Patent: Feb. 25, 2003

(54) METHIONINASE GENE THERAPY FOR TUMOR TREATMENT

(75) Inventors: Mingxu Xu, San Diego, CA (US); Yuying Tan, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

(21) Appl. No.: 09/195,055

(22) Filed: Nov. 18, 1998

Related U.S. Application Data

(60) Provisional application No. 60/104,474, filed on Oct. 16, 1998.

(51) Int. Cl.[7] ..................... A01N 43/04; A01N 61/00; C12N 15/00; C07H 21/04
(52) U.S. Cl. ..................... 424/93.2; 514/1; 514/2; 435/320.1; 536/23.2; 536/23.4; 424/93.1
(58) Field of Search ............... 514/44, 1, 2; 536/23.4, 536/23.2; 435/320.1, 325, 410; 424/93.1, 93.2

(56) References Cited

U.S. PATENT DOCUMENTS

| 5,690,929 A | 11/1997 | Lishko et al. ............... 424/94.5 |
| 5,715,835 A | 2/1998 | Lishko et al. ............... 128/898 |

FOREIGN PATENT DOCUMENTS

| WO | US93/11311 | 11/1993 |
| WO | WO 94/10323 | * 5/1994 |
| WO | WO 94 11535 | 5/1994 |
| WO | US96/09935 | 6/1996 |

OTHER PUBLICATIONS

Ludin et al., "Application of Novel Vectors for GFP–tagging of Proteins to Study Microtubule–associated Proteins," *Gene* (1996) 173:107–111.
Tan et al., "Serum Methionine Depletion Without Side Effects by Methioninase in Metastatic Breast Cancer Patients," *Anticancer Research* (1996) 16:3937–3942.
Huiyan Guo et al., "Methionine Depletion Modulates the Antitumor and Antimetastatic Efficacy of Ethioine", Anticancer Research 16:2719–2724 (1996).
Yuying Tan et al. "Anticancer Efficacy of Methioninase in Vivo", Anticancer Research 16:3931–3936 (1996).
Takayuki Yoshioka et al., "Anticancer Efficacy in Vivo and in Vitro, Synergy with 5–Fluorouracil, and Safety of Recombinant Methioninase", Cancer Research 58, 2583–2587, Jun. 15, 1998.
Wolfe et al, "Herpesvirus Vector Gene Transfer and Expression of β–glucuronidase in the Central Nervous System of MPS VII Mice", Nature Genetics, vol. 1, 379–384, Aug. 1992.
Kathleen L. Berkner, "Development of Adenovirus Vectors for the Expression of Heterologous Genes", BioTechniques, vol. 6, No. 7 (1988).
Yuying Tan et al., "Overexpression and Large–Scale Production of Recombinant L–Methionine–α–deamino–γ–mercaptomethane–lyase for Novel Anticancer Therapy", Protein Expression and Purification 9, 233–245 (1997).
Xiaoen Wang et al., "A New Patient–like Metastatic Model of Human Cancer Constructed . . . " Int. J. Cancer: 51, 992–995 (1992).
Xiaoen Wang et al., "A Patient–like Metastasizing Model of Human Lung Adenocarcinoma Constructed via Thoracotomy in Nude Mice", Anticancer Research 12: 1399–1402 (1992).
Huiyan Guo et al., "Therepeutic Tumor–Specific Cell Cycle Block Induced by Methioine Starvation in Vivo", Cancer Research 53: 5676–5679, Dec. 1, 1993.
Richard G. Vile et al., "Systemic Gene Therapy of Murine Melanoma Using Tissue Specific Expression of the HSVtk . . . ", Cancer Research 54: 6228–6234, Dec. 1, 1994.
Michael C. Alley et al., "Feasibility of Drug Screening with Panels of Human Tumor Cell Lines Using a Microculture Tetrazolium Assay", Cancer Research 48: 589–601, Feb. 1, 1988.
Robert M. Hoffman et al., "Reversible Growth Arrest in Simian Virus 40–Transformed Human Fibroblasts", Proc. Natl. Acad. Sci., vol. 77, No. 12, 7306–7310, Dec. 1980.
Curtis C. Harris, "Structure and Function of the p53 Tumor Suppressor Gene: Clues for Rational Cancer Therapeutic Strategies", Journal of the National Cancer Institute, vol. 88, No. 20, Oct. 16, 1996.
F. Breillout et al., "Methionine Dependency of Malignant Tumors: A Possible Approach for Therapy", Journal of the National Cancer Institute, Oct. 17, 1990, vol. 82, 20: 1628–1632.
J.A. Roth et al., "Retrovirus–mediated Wild–type p53 Gene Transfer to Tumors of Patients with Lung Cancer", Nature Medicine, vol. 2, Sep. 1996, 9:985–991.
Narihide Goseki et al., "Antitumor Effect of Methionine–Depleting Total Parenteral Nutrition With Doxorubicin Administration on Yoshida Sarcoma–Bearing Rats", Cancer, Apr. 1, 1992, vol. 69, No. 7.

(List continued on next page.)

*Primary Examiner*—Scott D. Priebe
*Assistant Examiner*—Shin-Lin Chen
(74) *Attorney, Agent, or Firm*—Morrison & Foerster LLP

(57) ABSTRACT

A depletion method to inhibit tumor growth includes introducing a viral expression system capable of expressing methioninase or a fusion protein containing methioninase into a tumor contained in a vertebrate subject or cells thereof. The fusion protein may contain a fluorescent protein to permit monitoring of the completeness of the depletion method. The fusion protein can be used in vivo as well as in vitro screening protocols which employ the viral expression system. The expression system includes control sequences and means to integrate the nucleotide sequence into the genome of a host cell for expression. The method may also include treating the cells with isolated methioninase and/or with a therapeutic cell. The depletion method can be with other known therapies, such as maintaining the animal having the tumor on a methionine depleted diet.

11 Claims, No Drawings

OTHER PUBLICATIONS

Hidehiko Tanaka et al., "Properties of L–Methionine γ–Lyase from Psuedomonas Ovalis", Biochemistry, vol. 16, No. 1, 1977.

Ken N. Wills et al., "Development and Characterization of Recombinant Adenoviruses Encoding Human p53 for Gene Therapy of Cancer", Human Gene Therapy, 5:1079–1088, Sep. 1994.

Leslie A. Lesoon–Wood et al., "Systemic Gene Therapy with p53 Reduces Growth and Metastases of a Malignant Human Breast Cancer in Nude Mice", Human Gene Therapy, 6:395–405, Apr. 1995.

Narihide Goseki et al., "Synergistic Effect of Methioine–depleting Total Parenteral Nutrition with 5–Fluorouracil on Human Gastric Cancer . . . " Japanese Journal of Cancer Research, 86, 484–489, May 1995.

Sami Loimas et al., "Herpes Simplex Virus Thymidine Kinase–Green Fluorescent Protein Fusion Gene: New Tool for Gene Transfer Studies and Gene Therapy", BioTechniques, vol. 24, No. 4 (1998).

Eck et al., Gene–Based Therapy, General Principles, Section 1, pp. 77–101.*

Verma et al., Gene therapy–promise, probels and propects, Nature, vol. 389, Sep. 18, 1997, pp. 239–242.*

Crystal, Transfer of Genes to Humans: Early Lessons and Obstacles to Success, Science 1995, vol. 270, pp. 404–410.*

Miller et al., Target vector for gene therapy, The FASEB Journal, Feb. 1995, vol. 9, pp. 190–199.*

Deonarain, Ligand–targeted receptor–mediated vectors for gene delivery, Ashely Publications Ltd., 1998, pp. 53–69.*

Rudinger et al., Characteristics of the amino acids as components of a peptide hormone sequence, Biological Council, Jun. 1976, pp. 1–7.*

Kaye et al., A singel amino acid substitution results in a retinoblastoma protein defective in phosphorylation and oncoprotein binding, Sep. 1990, Proc. Natl. Acad. Sci., vol. 87, pp. 6922–6926.*

Jolly, Viral vector system for gene therapy, 1994, Cancer Gene Therapy, vol. 1, No. 1, pp. 51–64.*

Douglas et al., Nature Biotechnology, vol. 14, p. 1574–1578, Nov. 1996.*

* cited by examiner

```
                       SEQUENCE LISTING

<160> NUMBER OF SEQ ID NOS: 4

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
ccgctcgaga tgcacggctc caacaagctc cca                                 33

<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
cgcggatcca ttaggcactc gccttgagtg cctg                                34

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3
ggaagatcta tgcacggctc caacaagctc ccagga                              36

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
ttaggcactc gccttgagtg cctg                                           24
```

METHIONINASE GENE THERAPY FOR TUMOR TREATMENT

This application claims priority benefit of Provisional U.S. Patent Application Ser. No. 60/104,474, filed Oct. 16, 1998.

TECHNICAL FIELD

The invention relates to protocols for the treatment of tumors. More specifically, the invention concerns insertion of a methioninase gene into tumor cells, optionally in combination with administration of methioninase, methionine deprivation or administration of a chemotherapeutic agent.

BACKGROUND ART

Various approaches to tumor treatment using gene replacement or other genetic therapy protocols have been suggested and verified in animal models. For example, since it is known that the p53 gene is a tumor suppressor (Harris, C. C., *JNCI* (1996) 88:1442–1445), the antitumor effects of p53 gene transfer have been explored. Successful results for tumors which contain defective p53 genes have been shown by Roth, J. A., et al., *Nat Med* (1996) 2:985–991 using retrovirus-mediated gene transfer in patients with lung cancer. Adenoviral vectors encoding p53 for gene therapy have been described by Wills, K. N., et al., *Hum Gene Ther* (1994) 5:1079–1088. An animal model of malignant human breast cancer in nude mice was shown to respond to adenoviral-mediated delivery of p53 by Lesoon-Wood, L. A., et al., *Hum Gene Ther* (1995) 6:395–405.

Alternatively, the Herpes simplex virus thymidine kinase gene (HSV-tk) in combination with gancyclovir has been shown to inhibit tumor growth in melanoma mode by Vile, R., et al. *Cancer Res* Dec. 1 (1994); 54(23):6228–34. However, surrounding cells may also be killed using such protocols in a "bystander" effect.

It is now well known that most tumor cells, in contrast to normal cells, are dependent on an external supply of methionine due to a high demand for methylation reactions. Thus, more methionine is required than is available from the endogenous synthesis route from homocysteine. Cancer cells arrest when exogenous methionine is unavailable in the late $S/G_2$ phase of the cell cycle (Hoffman, R. M., et al., *Proc Natl Acad Sci USA* (1980) 77:7306–7310.

Deprivation of methionine in the diet has been shown both in animal models and in the clinic to extend survival time (Breillout, F., et al., *JNCI* (1990) 82:1628–1632; Goseki, N., et al, *Cancer* (1992) 69:1865–1872; Hosiya, Y., et al., *Anticancer Res* (1996) 16:2719–2724; Guo, H., et al., *Cancer Res* (1993) 53:5676–5679; Goseki, N., et al., *Japan J Cancer Res* (1995) 86:484–489). In addition, administration of recombinant methioninase (rMETase) has been found to have antitumor efficacy both in vitro and in vivo (U.S. Pat. No. 5,690,929; Tan, Y., et al., *Anticancer Res* (1996) 16:3931–3936; Yoshioka, T., et al., *Cancer Res* (1998) 58:5283–5287). Methioninase is also known to deplete homocysteine levels, thus reducing the concentration of the endogenous precursor for methionine (U.S. Pat. No. 5,715,835).

It has now been found that the efficacy of methionine reduction protocols, including treatment with methioninase, can be enhanced and improved by introducing an expression system for the methioninase gene into tumor cells. Thus, the present invention is directed to gene therapy for tumor cell inhibition by supplying the METase gene.

DISCLOSURE OF THE INVENTION

The invention provides a distinct approach to antitumor therapy. Tumor cells are provided an expression system for methioninase, thus permitting an endogenous mechanism for further depleting needed methionine. The expression system can be utilized as the sole method of treatment, but is preferably used in combination with administration of METase protein, methionine depletion in the diet, and/or administration of a chemotherapeutic agent, such as 5-fluorouracil.

Accordingly, in one aspect, the invention is directed to a method to inhibit tumor growth which method comprises treating the cells of said tumor with a composition comprising a nucleic acid molecule, which nucleic acid molecule comprises; in a preferred embodiment, an expression system for a protein having methioninase activity along with a means for effecting the entry of said nucleic acid molecule into the tumor cells. The tumor cells may reside in a vertebrate animal; under those circumstances, the composition is a pharmaceutical or veterinary composition applied to the vertebrate. Preferred vertebrate subjects are mammals, such as primates, including humans, domestic animals, and rodents as well as avians, such as chickens, ducks and geese. The administration of the pharmaceutical or veterinary composition may be supplemented with administration of a protein with methioninase activity and/or placing the animal under a methionine-depleted diet and/or administering to the animal a chemotherapeutic agent.

In another aspect, the invention is directed to tumor cells modified to contain an expression system for production of a protein with methioninase activity. In another aspect, the invention is directed to a nonhuman animal comprising the modified tumor cells. The invention is also directed to adenoviral vectors which comprise the nucleotide sequence encoding methioninase.

In still other aspects, the invention is directed to a method to monitor the expression of methioninase in tumor cells which method comprises assessing the fluorescence of tumor cells that have been treated with an expression system for a fusion protein, said fusion protein comprising an amino acid sequence conferring methioninase activity linked to an amino acid sequence which effects emission of fluorescent light. The fluorescence may be observed in vitro or in vivo, even in the live animal.

MODES OF CARRYING OUT THE INVENTION

The invention provides uniquely effective protocols and materials for treatment of methionine-dependent tumors, as well as assay systems for monitoring the production of METase in tumor cells or in cells generally. The treatment method is selective for tumor cells, since tumor cells are methionine-dependent, whereas normal cells are not.

The expression systems employed in the present invention generally comprise a nucleotide sequence encoding a protein with methioninase activity operably linked to sequences which effect expression of the coding sequence. Alternatively, vectors for delivery of the nucleotide sequence encoding methioninase may be supplied which effect the insertion of the nucleotide sequence into the genome of the host, thus employing the endogenous control sequences to effect expression. The nucleotide sequence is, in this case, coupled to sequences which effect homologous recombination at known targets in the genome, or, alternatively, random integration into the genome may be relied upon. The inclusion of the expression system in a retroviral vector will serve this purpose as well. Use of viral vectors containing an expression system for the methioninase protein is a preferred means of administration.

Since tumor cells are rapidly dividing cells, retroviral vectors can conveniently be used to deliver the methioninase gene. However, other methods for transfecting such cells may also be employed. For example, Herpes simplex vectors can be employed for this purpose. Wolfe, J. H., et al., *Nature Genetics* (1992)1:379–384. A particularly preferred viral vector is based on adenovirus. Particularly preferred are adenovirus of Type 2 or Type 5 (Ad2 or Ad5). These viruses are not oncogenic and are relatively stable and easy to manipulate. The complete genomes of these types of adenovirus are known and there are a number of known mutants that have been made available for genetic therapy in general. Berkner, K. L., *Biotechniques* (1988) 6:612–629. However, while viral-based vectors are preferred, any suitable vector for transformation can be employed.

If viral vectors are used, the specificity of infectivity can be enhanced by including receptor-binding moieties in the vector. It is known in the art to modify viral surface molecules with binding domains of ligands, such as erythropoietin which targets erythroleukemia, heregulin which targets breast cancer and neurotensin which targets the colon.

If the vector contains an expression system suitable promoters and enhancers can be used. General constuitive promoters such as SV40 or CMV promoters can be included, along with their enhancer elements, or tissue-specific promoters may be used to enhance specificity. For example, the a fetal protein (AFP) promoter is specific to liver cells and is thus useful when the target tumor is a hepatoma; prostate-specific antigen (PSA) promoter is specific for prostate gland and thus suitable for administration to treat prostate cancer; the carcinoembryonic antigen (CEA) promoter is more general and is effective in cancers of the pancreas, lung, breast and colon.

Means to construct suitable vectors for delivery of the methioninase gene along with provision for its expression are well known in the art.

In order to effect the modification of tumor cells for production of methioninase, the expression system or integrating encoding nucleotide sequence must be formulated so as to enter the cell. Integration of the desired nucleotide sequences into viral vectors, such as adenovirus provides this means of entry. However, retroviral vectors, or other mediators of cellular uptake, such as lipids, or various liposomal type compositions or emulsions may also be employed.

The composition, comprising a nucleotide sequence encoding a protein with methioninase activity, preferably operably linked control sequences, or sequences effecting genomic integration, thus also contains a means for effecting cellular uptake. This composition is supplied to tumor cells, either in vitro or in vivo. In vitro administration is particularly helpful in assessing, in advance, the efficacy of the therapeutic approach for a particular individual, as well as expression levels of the methioninase in the tumor cells. For the latter purpose, it is advantageous to employ the protein having methioninase activity as a fusion protein to a reporter amino acid sequence, most preferably an amino acid sequence which confers fluorescence on the fusion protein. The use of green fluorescent protein (GFP) to confer fluorescence on a fusion protein is well understood in the art; see, for example, Chalfie, M., et al., *Science* (1994) 263:802–805. The use of green fluorescent protein to monitor metastasis of tumor cells in living subjects is described in U.S. Ser. No. 08/848,539 filed Apr. 28, 1997, now U.S. Pat. No. 6,232,523, and incorporated herein by reference.

While effecting endogenous expression of METase in tumor cells may be used alone if sufficient levels of expression are obtained, the protocol is most effective when combined with additional therapeutic approaches, such as administration of methioninase per se, administration of a methionine-depleted diet, and/or an additional chemotherapeutic agent. Suitable chemotherapeutic agents include, for example, 5-fluorouracil, leucouorin, cisplatin, vinca alkaloids, taxanes and nitrosoureas. A variety of chemotherapeutic agents is well known in the art.

Techniques for administering methioninase itself, for providing a methionine-depleted diet, and for providing chemotherapeutic agents are, of course, well known in the art.

The following examples are intended to illustrate but not to limit the invention.

Preparation A

Construction of Retroviral Vectors

Retroviral vectors comprising expression systems for either METase-GFP fusion protein or, as a control, GFP per se, were constructed. pLXSN (Clontech, Palo Alto, Calif.) was used as the host retroviral expression vector; the sequence encoding GFP was obtained from pEGFPC-3 described by Chalfie, M., et al., *Science* (1994) 263:802–805. The METase gene from *Pseudomonas putida* was obtained from pAC1 described in Tan, Y., et al., *Protein Expr. Purif.* (1997) 9:233–245. The construction was as follows:

The nucleotide sequence encoding METase was amplified by PCR from pAC1 using the primers

5'-CCGCTCGAGATGCACGGCTCCAACAAGCTCC-CA-3' (SEQ ID NO:1)

5'-CGCGGATCCATTAGGCACTCGCCTTGAGTGCC-TG-3' (SEQ ID NO:2)

The resulting 1.2 kb METase encoding DNA was ligated into pEGFPC-3 downstream of the XhoI/BamHI site. The resulting plasmid was digested with NheI, blunt ended, digested by BamHI and ligated into pLXSN which had been digested with HpaI, blunt ended and digested with BamHI. In the resultant vector, pGFP-METase, the GFP-METase gene was driven by the Moloney murine leukemia virus long terminal repeat (LTR) and a neomycin-resistance gene (NeoR) was driven by the simian virus 40 (SV40) early promoter.

The control vector, pGFP, was constructed by inserting the EGFP gene obtained from pEGFP-1 (Clontech) into the pLXSN retroviral vector. Briefly, pEGFP-1 was digested with NotI, blunted by Klenow polymerase and digested with EcoRI; the EGFP gene was separated by purified by low melting agarose electrophoresis. The pLXSN retroviral vector was digested with XhoI, blunted with Klenow and digested with EcoRI. The EGFP gene was then ligated into the digested vector to obtain pGFP.

NIH-3T3 based packaging cells expressing the 10A1 viral envelope, designated PT67 (Clontech, Palo Alto, Calif.), were cultured in DMEM/10% FBS/Pen/Strep. The resulting cells, grown to 70% confluence in 6-well culture dishes, were transfected with DOTAT™ (Boehringer-Manheim) liposomal reagent containing saturating amounts of either pGFP or pGFP-METase. The medium was replaced after 18 hours and stable virus-producing cells were selected by culturing for two weeks in the presence of 0.8 mg/ml G418 beginning two days after transfection. The supernatants contain the desired viral vectors designated vGFP-MET or vGFP, respectively.

EXAMPLE 1

Modified Tumor Cells

H460 is a human nonsmall cell lung adenocarcinoma cell line and was maintained in RPMI 1640 with 10% FBS/Pen/Strep. After incubation to 20% confluence, H460 cells were washed and exposed for 12 hours to supernatants containing vGFP-MET or vGFP in a composition containing the supernatants at a 1:1 ratio with RPMI 1640. The composition further contains 10% FBS and 8 µg polybrene. Transduced cells were selected in fresh RPMI 1640 containing 400 µg/ml G418 and the expression levels were monitored by GFP fluorescence. Highly expressing clones were isolated using cloning cylinders and amplified. The GFP fluorescence was evenly distributed in cells modified with vGFP, but localized only in the cytoplasm and not in the nuclei in cells modified with vGFP-METase. No significant growth rate differences were observed.

H460 cells which showed significant expression levels were assayed for METase activity by the method of Tanaka et al., $Biochemistry$ (1977) pp.100–106. Briefly, $10^7$ cells were collected after trypsin-EDTA digestion; pellets were washed with PBS and diluted with 0.5 ml PBS followed by homogenizing by sonication for 1 minute. The sonicates were centrifuged at 14000 rpm for 10 minutes and 0.2 ml supernatant used for the METase assay. The assay used 1 ml 50 mM phosphate buffer, pH8.0 containing 10 µM pyridoxal phosphate and 10 mM methionine for 10 minutes at 37° C. The reaction was stopped with 0.5 ml 4.5% TCA and the suspension centrifuged at 13000 rpm for 5 minutes and 0.5 ml supernatants were added to 0.5 ml 0.5% 3-methyl-2-benzylthiazoline hydrazone in 1 ml 1 M sodium acetate, pH5.2. The reaction mixtures were incubated at 50° C. for 30 minutes and the $OD_{335}$ measured. One unit of enzyme is defined as the amount that catalyzes the formation of 1 µM α-ketobutyrate per minute.

METase activity was not detectable in H460 parent cells or in H460 cells modified to contain vGFP. Cells modified to contain vGFP-METase showed a specific activity of $2.4 \times 10^{-2}$ units/mg protein. Since recombinant METase has a specific activity of 20 units/mg protein, the METase is expressed as 0.1% of total protein.

The relative levels of methionine in modified and unmodified H460 cells was also determined. Cells modified to contain vGFP-METase contained only 25% of the methionine concentration as unmodified cells or cells modified to contain vGFP.

EXAMPLE 2

Inhibition of Cell Growth by Endogenously Produced METase

Growth inhibition was determined by the MTT assay described by Alley, M. C., et al., $Cancer Res$ (1988) 48:589–601. The cells (2000 cells/well) were plated in 96-well culture plates in 100 µL medium for 24 hours. Various concentrations of recombinant METase were added to each well and cytotoxicity measured using the MTT assay after 3 days.

The results showed that recombinant METase had a more dramatic effect on cells modified with vGFP-MET than on control cells. The $IC_{50}$ for H460 vGFP-METase cells was 0.065 units/ml; for untransformed H460, the $IC_{50}$ was 0.115 units/ml; and for H460-vGFP cells, $IC_{50}$ was 0.095 units/ml. The $IC_{50}$ represents the concentration of recombinant METase which results in 50% cell mortality. Further, in the presence of 0.08 units/ml of recombinant METase, vGFP-METase cell survival was 10% that of untreated cells; vGFP cell survival was 90% of that of untreated cells; and unmodified H460 cells were not affected by this concentration of recombinant METase.

EXAMPLE 3

Effect on Cell Survival In Vivo

H460-vGFP and H460-vGFP-METase tumors were grown subcutaneously in nude mice. Fragments 1 mm in diameter were obtained and implanted by surgical orthotopic implantation (SOI) on the left lung in 20 mice for each type of tumor according to the procedure set forth in Wang, X., et al., $Int J Cancer$ (1992) 51:992–995; Wang, W., et al., $Anticancer Res$ (1992) 12:1399–1402. Briefly, after isofluorene inhalation anesthesia, the mice were placed in a right-lateral position under a dissecting microscope and an oblique skin incision was made in the left chest wall, muscles were separated, and the fourth intercostal space was exposed. The left pleural cavity was entered by blunt dissection and tumor tissues sewed into the upper lobe using 7-0 surgical sutures. The pleural cavity was closed with 6-0 surgical sutures. Pneumothorax was relieved by removing air from the pleural cavity with a 3 cc syringe/25 gauge needle. The chest muscle and skin were closed.

Two days later, 100 units of recombinant METase were administered intraperitoneally into 10 mice in each group twice a day for 12 days. Survival time was evaluated by Kaplan-Myer analysis.

TABLE 1

| Tumor | rMETase | Survival Time (days) |
|---|---|---|
| H460-GFP | — | 23 |
| H460-GFP | 100 units | 22 |
| H460-GFP-METase | — | 27 |
| H460-GFP-METase | 100 units | 33 |

As shown in Table 1, the combination of endogenously produced METase and administration of METase resulted in survival time significantly longer than in mice which harbored tumors that did not produce METase. However, the tumor size and metastasis to opposite lungs among these groups were not statistically significantly different.

EXAMPLE 4

Preparation of Adenovirus Containing the METase Gene

The nucleotide sequence encoding methioninase was amplified from pAC1 using the primers:

5'-GGAAGATCTATGCACGGCTCCAACAAGCTCC-CAGGA-3'(SEQ ID NO:3)

5'-TTAGGCACTCGCCTTGAGTGCCTG-3'(SEQ D NO:4).

The resulting 1.2 kb methioninase encoding DNA was ligated into the adenoviral transfer vector adeno-QESTTM (Quantum, Montreal, Canada). This vector, which had been modified to contain the nucleotide sequence encoding green fluorescent protein to give PQB1AdCMV5GFP, was digested at the PmeI/BglH site and the methioninase sequence inserted downstream of the CMV5 promoter and-enhancer. The linearized recombinant transfer vector, along with QBI-viral DNA were cotransfected into A293 cells. After two to three rounds of plaque assay screening, pure recombinant infectious adenoviral particles which express methioninase at high levels were obtained.

EXAMPLE 5

In Vivo Administration

Human tumors were established in nu/nu athymic mice by subcutaneous xenografts. After the tumors reached a volume of 200 mm$^3$, a total of 6×10$^9$ plaque forming units of the infectious viral particles prepared in Example 4 were administered directly to the tumor in three divided doses every other day. Controls were provided vGFP described in Preparation A. Tumor growth is slowed in the mice administered methioninase-encoding adenovirus as compared to controls.

In an additional experiment, human tumors are implanted by surgical orthotopic implantation in nu/nu athymic mice. After permitting tumor growth, methioninase expressing adenovirus and control virus are administered i.v. or i.p.

What is claimed is:

1. A method to inhibit growth of a tumor contained in a vertebrate subject by depleting methionine intracellularly in cells within the tumor, which method comprises administering locally directly to the cells of said tumor to be inhibited in situ a retrovirus or adenovirus which contains an expression system comprising a nucleotide sequence encoding a methioninase, or a fusion protein thereof, operably linked to at least a viral promoter to effect expression in said tumor cells, whereby a functional methioninase is expressed intracellularly in said tumor cells and intracellular methionine within said tumor cells is thereby sufficiently depleted to reduce the tumor growth rate and enhance the chances of survival for the subject.

2. The method of claim 1, wherein the virus includes at least one receptor binding moiety.

3. The method of claim 1, further comprising treating the cells of the tumor with isolated methioninase to further deplete methionine concentration.

4. The method of claim 1, further comprising placing the subject on a methionine-depleted diet.

5. The method of claim 1, further comprising administering to the subject a chemotherapeutic agent.

6. The method of claim 1, wherein the subject is a mammal.

7. The method of claim 1, wherein the methioninase is expressed as about 0.1% of total tumor cell protein.

8. The method of claim 1, wherein the viral promoter is the CMV promoter, or promoter which is the MMLV-LTR.

9. The method of claim 8 wherein the fusion protein comprises methioninase fused to a green fluorescent protein (GFP).

10. The method of claim 1, wherein the fusion protein comprises methioninase fused to a fluorescent protein.

11. The method of claim 10, wherein the fluorescent protein is a green fluorescent protein (GFP).

* * * * *